United States Patent [19]
Suprise

[11] Patent Number: 5,853,405
[45] Date of Patent: Dec. 29, 1998

[54] DISPOSABLE ABSORBENT ARTICLE HAVING A GARMENT-LIKE APPEARANCE

[75] Inventor: Jody Dorothy Suprise, Neenah, Wis.

[73] Assignee: Kimberly-Clark Worldwide, Inc., Neenah, Wis.

[21] Appl. No.: 886,335

[22] Filed: Jul. 1, 1997

Related U.S. Application Data

[63] Continuation of Ser. No. 561,733, Nov. 22, 1995.
[51] Int. Cl.$^6$ ..................................................... A61F 13/15
[52] U.S. Cl. ........................................ 604/391; 604/385.1
[58] Field of Search .................................... 604/379, 383, 604/393, 385.1, 385.2

[56] References Cited

U.S. PATENT DOCUMENTS

| | | |
|---|---|---|
| 1,201,860 | 10/1916 | Nelke . |
| 2,028,602 | 1/1936 | Hanson ........................................... 2/70 |
| 2,839,057 | 6/1958 | Argyll ...................................... 128/288 |
| 3,368,562 | 2/1968 | Vogt ...................................... 604/385.1 |
| 3,727,238 | 4/1973 | Wolfson ........................................... 2/69 |
| 3,954,107 | 5/1976 | Chesky et al. ......................... 604/385.1 |
| 4,247,959 | 2/1981 | Rose .............................................. 2/212 |
| 4,280,230 | 7/1981 | LaFleur ....................................... 2/408 |
| 4,327,448 | 5/1982 | Lunt ............................................. 2/404 |
| 4,459,705 | 7/1984 | Langford .................................... 2/105 |
| 4,475,912 | 10/1984 | Coates .................................. 604/385.1 |
| 4,488,317 | 12/1984 | Polsky ......................................... 2/227 |
| 4,555,245 | 11/1985 | Armbruster ............................. 604/396 |

(List continued on next page.)

FOREIGN PATENT DOCUMENTS

| | | |
|---|---|---|
| 0217032 | 4/1987 | European Pat. Off. . |
| 620555 | 3/1949 | United Kingdom . |
| 636684 | 5/1950 | United Kingdom . |
| 2 112 268 | 7/1983 | United Kingdom . |
| 2273646 | 6/1994 | United Kingdom . |
| WO 91/08725 A1 | 6/1991 | WIPO .............................. A61F 13/15 |
| WO 92/12648 A1 | 8/1992 | WIPO .............................. A41B 13/04 |
| WO 96/03950 A1 | 2/1996 | WIPO .............................. A61F 13/15 |

OTHER PUBLICATIONS

U.S. Patent Application Serial No. 08/476,742 filed Jun. 7, 1995, by S. Gryskiewicz et al., entitled "Absorbent Article Including Liquid Containment Beams and Leakage Barriers."

U.S. Patent Application Serial No. 206,986 filed Mar. 4, 1994, by C. Ellis and D. Bishop, entitled "Fibrous Nonwoven Web Surge Layer for Personal Care Absorbent Articles and the Like."

U.S. Patent Application Serial No. 206,069 filed Mar. 4, 1994, by C. Ellis and R. Everett, entitled "Improved Surge Management Fibrous Nonwoven Web for Personal Care Absorbent Articles and the Like."

(List continued on next page.)

*Primary Examiner*—Mark O. Polutta
*Assistant Examiner*—Ki Yong O
*Attorney, Agent, or Firm*—Jeffrey B. Curtin

[57] ABSTRACT

A disposable absorbent article defines a first side portion, a second side portion, and a longitudinal centerline between the side portions. The absorbent article comprises an outer cover and an absorbent insert which is connected to the outer cover. The outer cover comprises a first side panel which is located in the first side portion of the absorbent article and a second side panel which is located in the second side portion of the absorbent article. An edge of the first side panel is connected to an edge of the second side panel to provide a seam which extends along the longitudinal centerline between the side portions of the absorbent article. The opposite waist regions on each side panel are configured to encircle the legs of the wearer and releasably engage together about the hips of the wearer. The disposable absorbent article has an aesthetically pleasing garment-like appearance and is readily refastenable about the hips of the wearer.

14 Claims, 7 Drawing Sheets

U.S. PATENT DOCUMENTS

| | | | |
|---|---|---|---|
| 4,631,062 | 12/1986 | Lassen et al. | 604/393 |
| 4,663,220 | 5/1987 | Wisneski et al. | 428/221 |
| 4,704,116 | 11/1987 | Enloe | 604/385 |
| 4,745,636 | 5/1988 | Lunt | 2/402 |
| 4,797,955 | 1/1989 | Garrett | 2/213 |
| 4,808,177 | 2/1989 | DesMarais et al. | 604/385.1 |
| 4,935,021 | 6/1990 | Huffman et al. | 604/385.2 |
| 5,052,058 | 10/1991 | Mueller | 2/228 |
| 5,226,992 | 7/1993 | Morman | 156/62.4 |
| 5,435,014 | 7/1995 | Moretz et al. | 604/393 |
| 5,451,217 | 9/1995 | Fujioka et al. | 604/385.1 |
| 5,476,458 | 12/1995 | Glaug et al. | 604/378 |
| 5,531,732 | 7/1996 | Wood | 604/385.2 |
| 5,546,607 | 8/1996 | Roberts | 604/385.2 |

OTHER PUBLICATIONS

U.S. Patent Application Serial No. 310,186 filed Sep. 21, 1994, by F. Chen et al. entitled "Wet Resilient Paper Sheets."

Patent Cooperation Treaty Search Report from the International Search Authority, International Application No. PCT/US96/17095 dated Mar. 20, 1997.

DISPOSABLE ABSORBENT ARTICLE HAVING A GARMENT-LIKE APPEARANCE

This application is a continuation of application Ser. No. 08/561,733 entitled "DISPOSABE ABSORBENT ARTICLE HAVING A GARMENT—LIKE APPEARANCE" and filed in the U.S. Patent and Trademark Office on Nov. 22, 1995. The entirety of this application is hereby incorporated by reference.

BACKGROUND OF THE INVENTION

1. Field of the Invention

The present invention relates to disposable absorbent articles which are adapted to contain body exudates. More particularly, the present invention relates disposable absorbent articles which have a garment-like appearance.

2. Description of the Related Art

Conventional disposable absorbent articles, such as disposable diapers, have typically included a bodyside liner, an outer cover, and an absorbent core disposed between the outer cover and the bodyside liner. Typically, the outer covers of such conventional absorbent articles have been constructed from a generally rectangular sheet of material which has had portions of its side margins removed. Thus, the end margins of the sheet of material provide the waist opening region of the absorbent article while the partially removed side margins provide the leg opening regions of the absorbent article. The outer covers of such absorbent articles have also been constructed with various types of elasticized portions at the waist and leg opening regions. Such elasticized portions have been used to reduce the leakage of body exudates from the absorbent article. The elasticized portions of the outer cover have also been used to improve the appearance and fit of the absorbent article about the wearer. For example, conventional disposable absorbent articles have generally utilized outer covers which have elastic strands positioned at the leg and waist opening regions to gather the outer cover and absorbent article to hold it against the body of the wearer.

However, conventional disposable absorbent articles which include outer covers as described above have exhibited several shortcomings. For example, it has been difficult to conform conventional absorbent articles and, in particular, the absorbent cores of such articles to the body of the wearer. Typically, the absorbent core on such conventional absorbent articles has been bonded to or immobilized between the outer cover and the bodyside liner. Consequently, it has been difficult to control the shape of the absorbent article to maintain an aesthetically pleasing appearance during use. In an attempt to better gather the absorbent core and the absorbent article, the waist and leg opening regions of conventional absorbent articles have included elastics which apply high contracting or gathering forces on the absorbent article. However, such high forces have undesirably resulted in irritation and red marking of the skin of the wearer. The high forces have also resulted in an undesirable level of bunching of the absorbent article especially in the crotch region.

To obtain a better fit and appearance about different sized wearers, it also has been required to provide conventional disposable absorbent articles in many different sizes. For example, it has been required to provide conventional disposable diapers in as many as 3–6 different sizes to accommodate different sized infants. As a result, the costs of manufacturing and marketing such articles has been undesirably high.

Despite the attempts to develop more aesthetically pleasing and improved disposable absorbent articles, there remains the need for disposable absorbent articles which contain body exudates while providing an optimum fit about the wearer and maintaining a pleasing appearance. Moreover, there is a need for a disposable absorbent article which has a garment-like appearance and which can be easily secured about and removed from the waist of a wearer.

SUMMARY OF THE INVENTION

In response to the difficulties and problems discussed above, a new disposable absorbent article which has a garment-like appearance has been discovered. In one aspect, the present invention concerns an outer cover which is adapted for use in a disposable absorbent article. The outer cover comprises two individual side panels. An edge of one side panel is connected to an edge of the opposite side panel to provide a seam which extends along a longitudinal centerline of the outer cover. Each of said side panels defines a pair of opposed waist regions which are releasably engageable together to define a leg opening in the outer cover. In a particular aspect, the seam extends substantially continuously along the entire length of the outer cover. The outer cover may also include a pair of concealment cuffs which are located along the side regions of the outer cover.

In another aspect, the present invention concerns a disposable absorbent article which defines a first side portion, a second side portion, and a longitudinal centerline between the side portions. The absorbent article comprises an outer cover and an absorbent insert which is connected to the outer cover. The outer cover defines a length, a pair of laterally opposed side regions, a pair of longitudinally opposed waist regions, and a crotch region which extends between and connects the waist regions. The outer cover comprises a first side panel which is located in the first side portion of the absorbent article and a second side panel which is located in the second side portion of the absorbent article. An edge of the first side panel is connected to an edge of the second side panel to provide a seam which extends along the longitudinal centerline between the side portions of the absorbent article. The opposite waist regions on each side panel are releasably engageable together to define a pair of leg openings in the outer cover.

In still another aspect, the present invention concerns a disposable absorbent article which defines a first side portion, a second side portion, and a longitudinal centerline between the side portions. The absorbent article comprises an outer cover which includes two individual side panels which are connected together to provide a seam which extends along the longitudinal centerline of the absorbent article. The absorbent article further comprises an absorbent insert which is connected to the outer cover. The absorbent insert defines a pair of longitudinally opposed end margins and a pair of laterally opposed side margins and includes a bodyside liner, a backsheet which is connected to the bodyside liner in a superposed relation, and an absorbent core which is located between the bodyside liner and the backsheet. In a particular aspect, the end margins of the absorbent insert are connected to the outer cover and the absorbent insert remains unconnected from the outer cover between the end margins. The absorbent core may include at least two independent, longitudinally extending absorbent strips. The absorbent article may also include a pair of longitudinally extending containment flaps which are located on the side margins of the absorbent insert.

In yet another aspect, the present invention concerns a method of making a disposable absorbent article which defines a first side portion, a second side portion, and a longitudinal centerline between said side portions. The method comprises: (a) cuffing a continuously moving web of material into a first side panel and a second side panel; (b) bonding an edge of the first side panel to an edge of the second side panel along a seam to provide an outer cover for the disposable absorbent article wherein said seam extends along the longitudinal centerline of the absorbent article; and (c) attaching an absorbent insert which includes a pair of longitudinally opposed end margins and a pair of laterally opposed side margins to the outer cover.

The present invention advantageously provides a disposable absorbent article which has a garment-like appearance and refastenable side seams which allow the article to be easily secured about and removed from the waist of the wearer. The disposable absorbent article of the different aspects of the present invention also achieves a good fit while maintaining an aesthetically pleasing appearance when compared to conventional absorbent articles which gather and bunch in the crotch region. Moreover, the disposable absorbent article of the present invention may also provide improved containment of body exudates within the absorbent area of the article by allowing the absorbent core to remain unattached from the outer cover in at least the crotch region of the article.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

Figure 1:
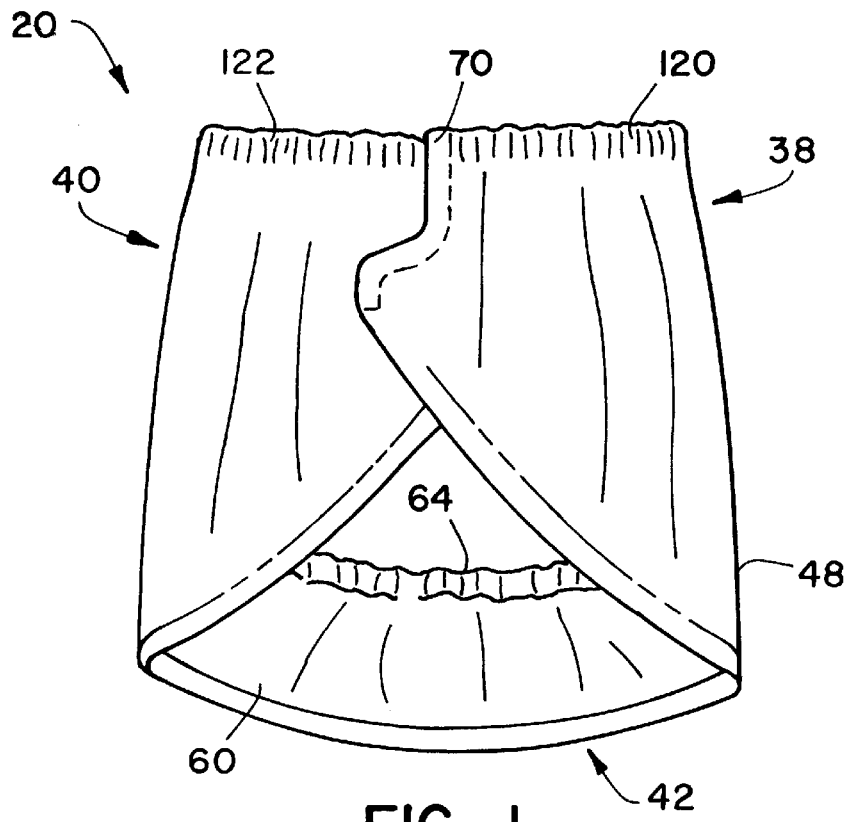
FIG. 1 representatively shows a side elevational view of an example of a disposable absorbent article according to the present invention.
Figure 2:
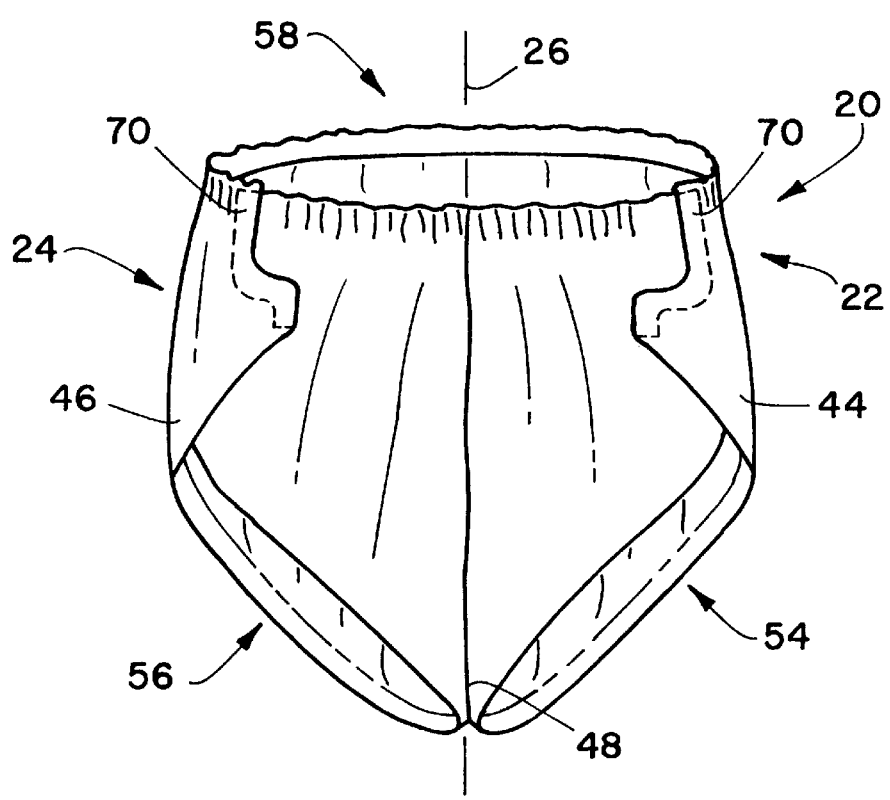
FIG. 2 representatively shows a front elevational view of the disposable absorbent article of FIG. 1.

The present invention concerns disposable absorbent articles which have a garment-like appearance. The disposable absorbent articles are adapted to be worn adjacent to the body of a wearer to absorb and contain various exudates discharged from the body. As used herein, the term "disposable" refers to articles which are intended to be discarded after a limited use and which are not intended to be laundered or otherwise restored for reuse. The disposable absorbent articles of the present invention will be described in terms of a disposable diaper article which is adapted to be worn by infants about the lower torso. It is understood that the disposable absorbent articles of the present invention are equally adaptable for use as other types of absorbent articles such as adult incontinent products, training pants, feminine hygiene products, other personal care or health care garments, and the like.

FIGS. 1–5 and 9–12 representatively illustrate alternative examples of disposable absorbent articles, as generally indicated at 20, according to the present invention wherein like numerals represent like elements. As representatively illustrated in FIGS. 1–5, the absorbent article 20 defines a first side portion 22 and a second side portion 24. As used herein, reference to a side portion refers to that part of the absorbent article which is generally located on the sides or hips of a wearer when in use. The absorbent article 20 also defines a longitudinal centerline 26 which extends along a longitudinal length of the absorbent article 20. The disposable absorbent article 20 includes an outer cover 30 and an absorbent insert 80 which is connected to the outer cover 30. The absorbent insert 80 is configured to contain and/or absorb any body exudates discharged from the wearer. Whereas, the outer cover 30 is configured to maintain the absorbent article about the waist of the wearer, conceal the absorbent insert from view, and provide the garment-like appearance.

The absorbent article 20 may also include a pair of concealment cuffs 60 which are connected to the outer cover and configured to hide the absorbent insert 80 from view. The absorbent article 20 may also include a pair of containment flaps 110 which are connected to the absorbent insert 80 and configured to hold and contain any body exudates within the absorbent insert 80 to avoid soiling the outer cover 30 of the absorbent article 20 and any other outer garments worn by the wearer. The illustrated absorbent article 20 further includes a fastening means which is intended to maintain the absorbent article 20 about the waist of the wearer when in use. It should be recognized that individual components of the absorbent article 20 may be optional depending upon the intended use of the absorbent article 20.

Figure 3:
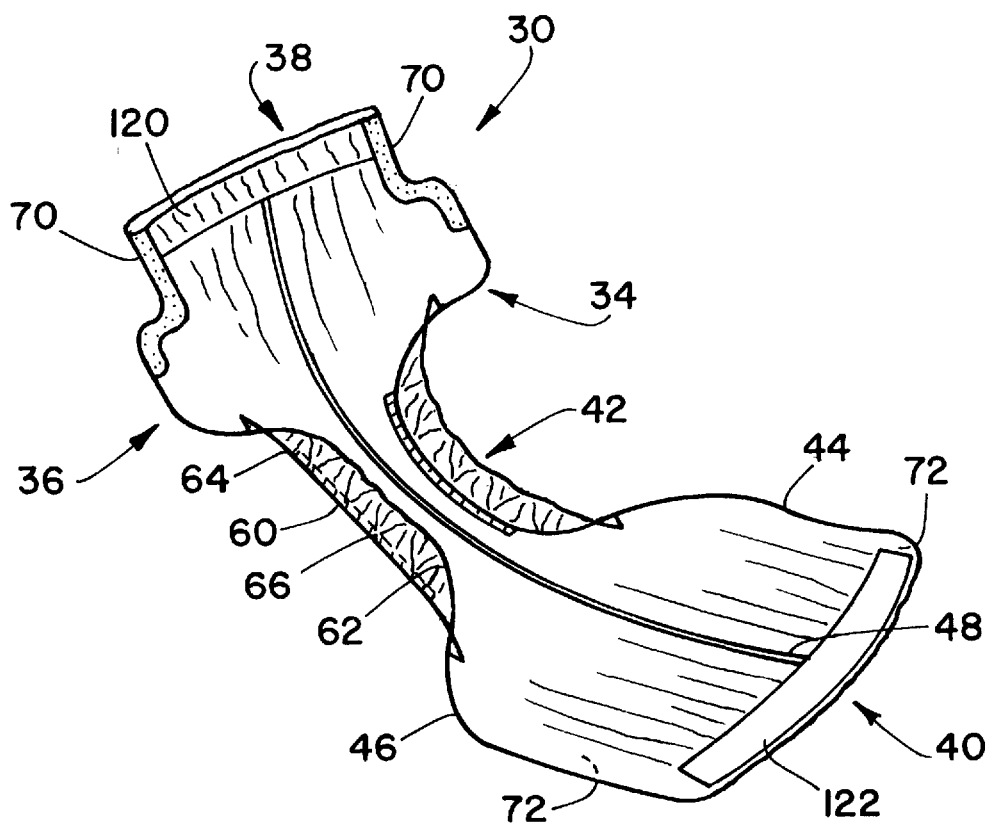
FIG. 3 representatively shows a perspective view of the outer cover of the disposable absorbent article of FIGS. 1 and 2 wherein the absorbent insert has been removed and the elastic members have contracted and gathered the edges of the outer cover.
Figure 5:
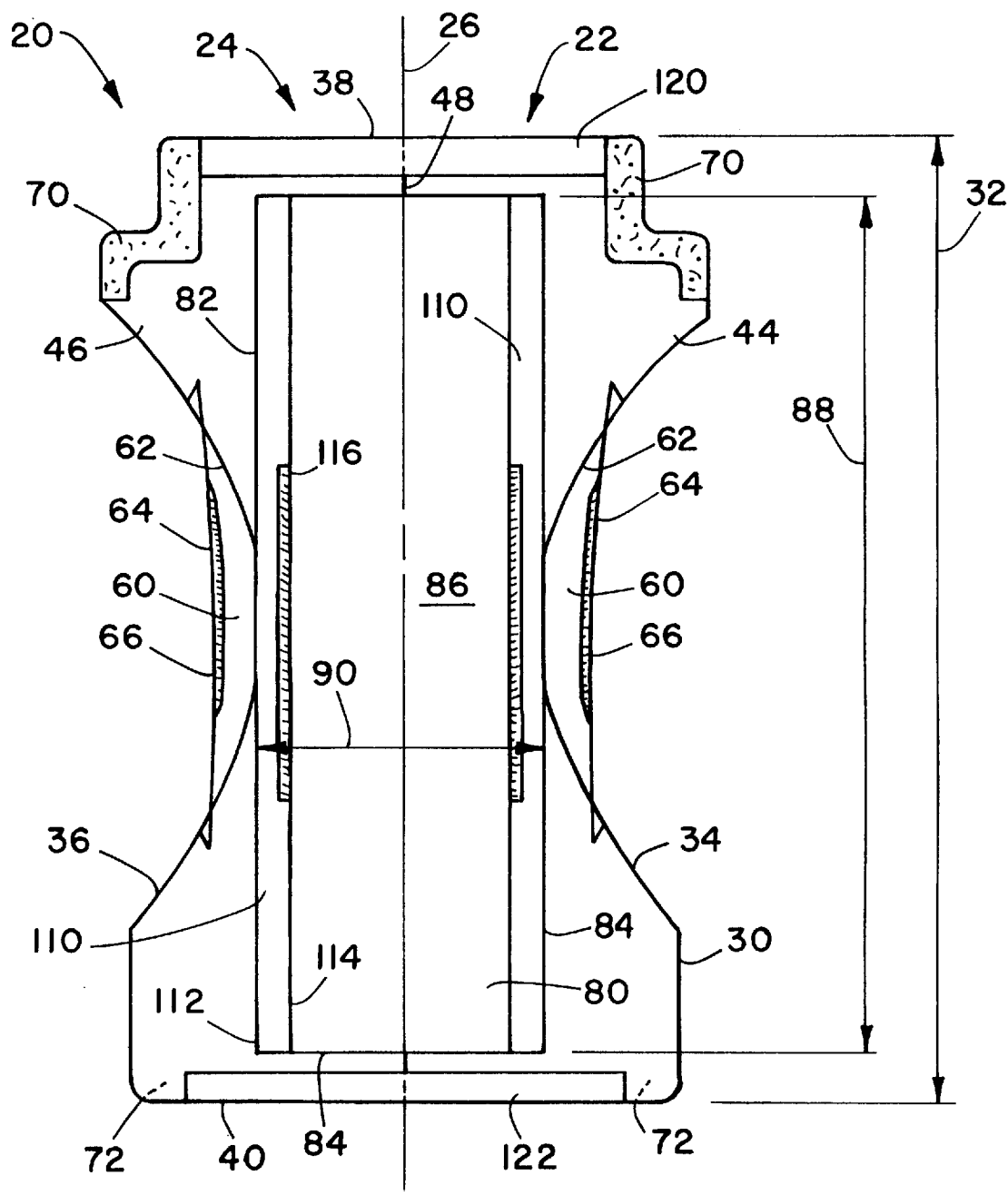
FIG. 5 representatively shows a plan view of the disposable absorbent article of FIGS. 1–4 in a stretched and laid flat condition with the surface of the article which contacts the wearer facing the viewer.

As representatively illustrated in FIGS. 3 and 5, the outer cover 30 of the absorbent article 20 defines a longitudinally extending length 32, a pair of laterally opposed side regions 34 and 36, a pair of longitudinally opposed waist regions 38 and 40, and a crotch region 42 which extends between and connects the waist regions. The edges of the side regions 34 and 36 of the outer cover 30 define leg openings 54 and 56 (FIG. 2) for the outer cover 30 which may be curvilinear. The waist regions 38 and 40 of the outer cover 30 define a waist opening 58 and comprise the upper portions of the absorbent article 20 when worn. The waist regions 38 and 40 are configured to wholly or partially cover or encircle the waist of the wearer when worn. The crotch region 42 of the outer cover 30 comprises the portion of the outer cover 30 which, when worm is positioned between the legs of the wearer and covers the lower torso of the wearer.

The representatively illustrated outer cover 30 comprises a first side panel 44 which is located in the first side portion 22 of the absorbent article 20 and a second side panel 46 which is located in the second side portion 34 of the absorbent article 20. An edge of the first side panel 44 is suitably connected to an edge of the second side panel 46 to provide a seam 48. The edges of the side panels 44 and 46 may be continuously connected together along the seam or, optionally, may be intermittently connected together along the seam 48. The seam 48 extends along the longitudinal centerline 26 of the absorbent article 20 between the side portions 22 and 24 of the absorbent article 20. The length of the seam 48 may or may not extend along the entire length 32 of the outer cover 30. Desirably, the seam 48 extends substantially continuously along the entire length 32 of the outer cover 30 to provide a more garment-like appearance to the absorbent article 20. In such a configuration, each side panel 44 and 46 defines a length which is substantially equal to the length 32 of the outer cover 30.

Figure 6:
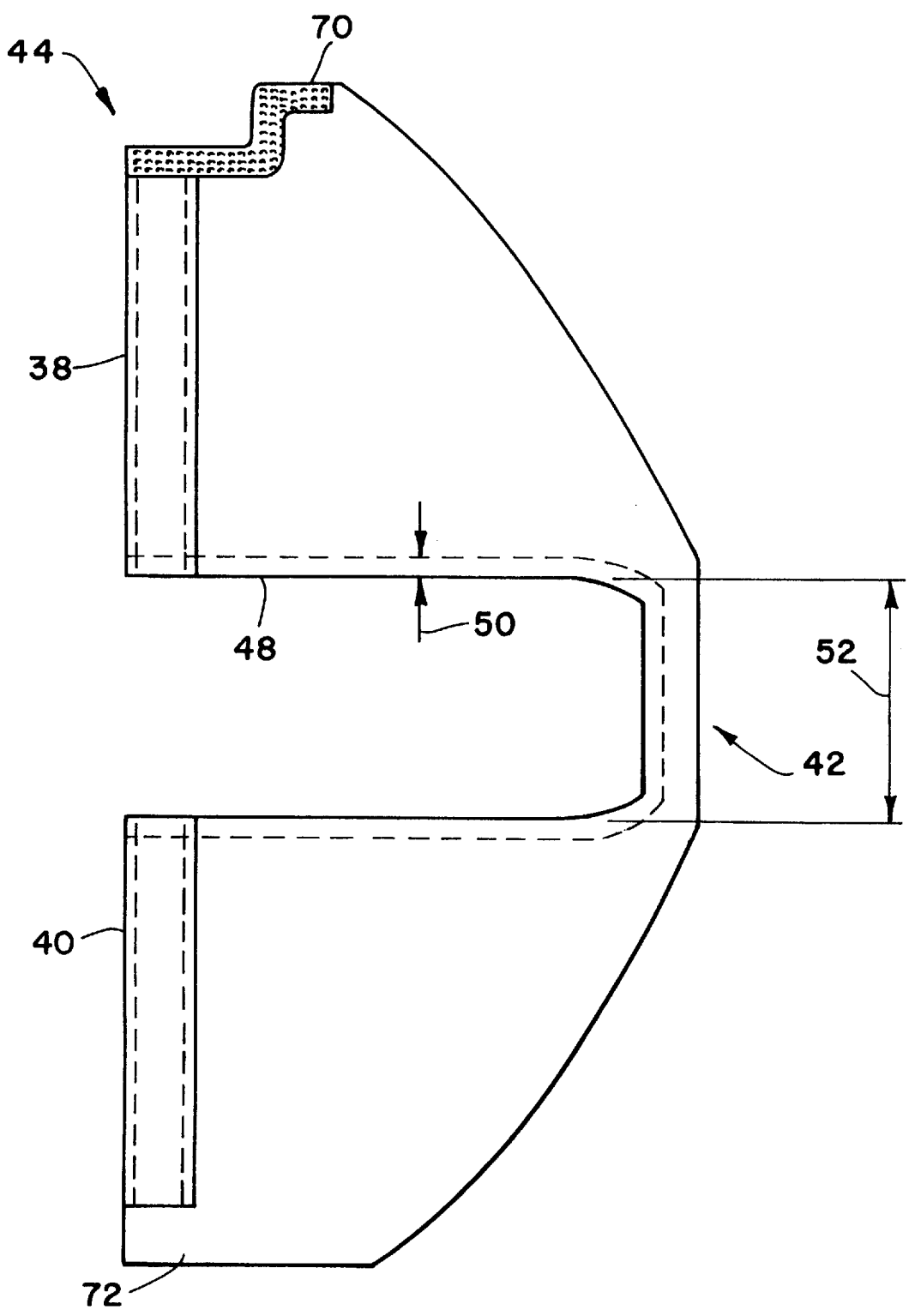
FIG. 6 representatively shows a plan view of one side panel of the outer cover of the disposable absorbent article of FIGS. 1–5 in a stretched and laid flat condition.

The side panels 44 and 46 of the outer cover 30 may have any configuration which provides the desired garment-like appearance to the absorbent article 20. Desirably, the side panels 44 and 46 are substantially identical for ease of manufacturing. FIG. 6 representatively illustrates an example of a pattern which can be used to provide the side panels 44 and 46. The pattern representatively illustrated defines one side panel 44. The portions of the pattern which corresponds to the seam 48, the waist regions 38 and 40, and the crotch region 42 of the outer cover 30 when assembled are also illustrated. The illustrated side panel 44 also defines the length 52 of the crotch region 42 of the outer cover 30. The crotch length 52 will vary depending upon the size of the wearer. Desirably, the crotch length 52 is at least about 15 percent and more desirably at least about 20 percent of the length 32 of the outer cover 30 to provide a more garment-like appearance with less bunching in the crotch region when compared to conventional absorbent articles. When the disposable absorbent articles is intended to be worn by an infant weighing from about 30 to about 35 pounds, the crotch length 52 is generally from about 5 to about 15 centimeters, desirably at least about 8 centimeters, and more desirably at least about 10 centimeters.

The seam 48 between the side portions 22 and 24 of the absorbent article 20 is typically constructed by positioning the edges of the side panels 44 and 46 in an overlapping arrangement and suitably connecting them together. The amount of overlap of the edges of the side panels 44 and 46 can be varied to provide any desired width 50 (FIG. 6) of the seam 48. For example, the seam 48 may define a width 50 of from about 0.3 centimeters to about 1.9 centimeters. Desirably, the seam 48 defines a width 50 of at least about 0.64 centimeters and more desirably at least about 1.3 centimeters to provide a more garment-like appearance to the disposable absorbent article 20 and an increased strength to the outer cover 30 along the seam 48. The edges of the side panels 44 and 46 may be connected together to provide the seam 48 in any of several ways which are well known to those skilled in the art. For example, the edges of the side panels 44 and 46 may be ultrasonically bonded, thermally bonded or adhesively bonded together to provide the seam 48.

Applicants have discovered that disposable absorbent articles which are constructed to have a seam which extends along a longitudinal centerline of the article, as described in the present invention, provide a more optimum fit about the wearer and a more garment-like appearance when compared to conventional absorbent articles. In particular, the incorporation of a seam along the longitudinal centerline of the article provides an improved fit and appearance of the crotch region and waist regions which are not constricted by the crotch region.

The outer cover 30 of the absorbent article 20 may suitably be composed of a material which is either liquid permeable or liquid impermeable. Since the absorbent insert 80 of the different aspects of the present invention is designed to contain the body exudates discharged from the wearer, it is generally not necessary that the outer cover 30 be liquid impermeable. For example, the outer cover 30 may include various woven or nonwoven materials such as spunbond material, meltblown material, cotton material, rayon material or combinations thereof such as a spunbond-meltblown-spunbond (SMS) laminate material. The outer cover 30 may also be an elasticized material such as a stretch-thermal laminate (STL), neck-bonded laminate (NBL), or stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference.

The outer cover 30 may also be at least partially liquid impermeable to further prevent any leakage of body exudates. For example, a typical outer cover 30 can be manufactured from a thin plastic film or other flexible liquid-impermeable material. In a particular aspect, the outer cover 30 may be formed from a polyethylene film having a thickness of from about 0.012 millimeter (0.5 mil) to about 0.051 millimeter (2.0 mils). If it is desired to present the outer cover 30 with a more clothlike feeling, the outer cover 30 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). The outer cover 30 may also be a stretch-thermal laminate (STL) material which includes a meltblown film layer positioned between two spunbond layers and which has a basis weight of about 73 grams per square meter. The meltblown film layer may be composed of meltblown polypropylene fibers and the spunbond layers may be composed of polypropylene fibers. The outer cover 30 may also include bicomponent fibers such as polyethylene/polypropylene bicomponent fibers. Methods of forming such clothlike outer covers are known to those skilled in the art. Further, the outer cover 30 may be formed of a woven or nonwoven fibrous web layer which has been totally or partially constructed or treated to impart a desired level of liquid impermeability to selected regions. Still further, the outer cover 30 may optionally be composed of a micro-porous "breathable" material which permits vapors to escape from the absorbent article 20 while still preventing liquid exudates from passing through the outer cover 30.

As representatively illustrated in FIGS. 1–5, the outer cover 30 of the disposable absorbent article 20 may include a pair of concealment cuffs 60 which are configured to hide the absorbent insert 80 and provide an additional barrier to the lateral flow of body exudates. The concealment cuffs 60 are located along the laterally opposed side regions 34 and 36 of the outer cover 30. Each concealment cuff 60 defines a fixed edge 62 and a free edge 64. Each of the concealment cuffs 60 may also include at least one elongated elastic member 66 which is attached to the free edge 64 of the concealment cuff 60 and configured to gather the concealment cuff 60 when it is relaxed. The concealment cuffs 60 may extend longitudinally along the entire length 32 of the outer cover 30 or may only extend partially along the length of the outer cover 30. When the concealment cuffs 60 are shorter in length than the outer cover 30, the concealment cuffs 60 can be selectively positioned anywhere along the side regions 34 and 36 of the outer cover 30. In a particular aspect of the invention, the concealment cuffs 60 are positioned along the side regions 34 and 36 primarily in the crotch region 42 of the outer cover 30.

The concealment cuffs 60 can be made from any material which provides the desired concealment of the absorbent insert 80 and, optionally, an additional barrier to the lateral flow of body exudates. For example, the concealment cuffs 60 may be constructed of a material which is similar to the material comprising the outer cover 30. Other conventional materials, such as polymer films, may also be employed. In a particular aspect, the concealment cuffs 60 may be constructed of a STL material composed of a meltblown polypropylene layer between two spunbond layers and having a basis weight of about 73 grams per square meter.

Each concealment cuff 60 is attached to the side regions 34 and 36 of the outer cover 30 such that the concealment cuffs 60 effectively hide or conceal the absorbent insert 80 from view as is representatively illustrated in FIG. 1. The fixed edge 62 of each of the concealment cuffs 60 is attached to the side regions 34 and 36 of the outer cover 30 while the free edge 64 of each of the concealment cuffs 60 remains unattached from the outer cover 30 in at least the crotch region 42 of the outer cover 30. The fixed edge 62 of the concealment cuffs 60 may be attached to the outer cover 30 in any of several ways which are well known to those skilled in the art. For example, the fixed edge 62 of the cuffs 60 may be ultrasonically bonded, thermally bonded or adhesively bonded to the side regions 34 and 36 of the outer cover 30. The free edge 64 of each of the concealment cuffs 60 is generally aligned parallel to the longitudinal centerline 26 of the absorbent article 20. In a particular aspect, the free edge 64 of each concealment cuff 60 remains unattached from the side regions 34 and 36 of the outer cover 30 along substantially the entire length of the free edge 64 to provide improved performance.

Each concealment cuff 60 is also configured such that the free edge 64 of the concealment cuff 60 tends to position itself in a spaced relation away from the outer cover 30 toward a generally upright and perpendicular configuration, especially in the crotch region 42 when in use. As representatively illustrated in FIG. 1, the free edge 64 of each concealment cuff 60 is desirably spaced away from the outer cover 30 when in use thereby hiding or concealing the absorbent insert 80 from view. Desirably, the free edge 64 of each concealment cuff 60 maintains a contacting relationship with the body of the wearer while the outer cover 30 may be spaced away from the body of the wearer when in use. Typically, an elastic member 66 is attached to the free edge 64 of each concealment cuff 60 to maintain the spaced away relationship between the free edge 64 and the outer cover 30. For example, the elastic member 66 may be attached to the free edge 64 in an elastically contractible condition such that the contraction of the elastic member 66 gathers or contracts and shortens the free edge 64 of the concealment cuff 60 to achieve the desired spaced away relationship.

Materials suitable for use as the elastic member 66 of the concealment cuffs 60 are known to those skilled in the art. Exemplary of such materials are sheets, strands or ribbons of a polymeric, elastomeric material which are adhered to the cuffs 60 in a stretched condition, or which are attached to the cuffs 60 while the cuffs are pleated, such that elastic constrictive forces are imparted to the cuffs. The elastic member 66 may also include such materials as polyurethane, synthetic and natural rubber. In a particular aspect of the invention, the elastic members 66 may be composed of a plurality of individual strands of 620 decitex Lycra® which are commercially available from E. I. DuPont de Nemours Co., a business having offices in Wilmington, Del. The concealment cuffs 60 may include from 1 to about 10 elastic strands along the free edge 64.

The elastic members 66 may be elongated prior to being attached to the free edge 64 of the concealment cuffs 60. For example, the elastic members 66 may be elongated at least about 75 percent and desirably from about 100 to about 150 percent before being attached such that the elastic members 66 gather the free edge 64 of the concealment cuffs 60. Since the main purpose of the concealment cuffs 60 is to hide the absorbent insert 80 from view, it is not required that the free edge 64 form a tight seal about the body of the wearer. Accordingly, it is desirable that the elastic members 66 be elongated no more than about 150 percent and more desirably no more than about 125 percent before being attached to the concealment cuffs 60. Moreover, it is desirable that the elastic member 66 exerts a tension of no more than about 150 grams and desirably no more than about 90 grams on the free edge 64 of the concealment cuff 60 when the free edge 64 of the concealment cuff 60 is in a longitudinally extended position. Such low levels of elongation and tension effectively maintain the free edge 64 in a spaced away relation from the outer cover 30 while not undesirably irritating the legs of the wearer. The elastic members 66 may be joined to the concealment cuffs 60 by any means known to those skilled in the art. For example, adhesive, thermal or ultrasonic bonding techniques may be used to join the elastic members 66 to the concealment cuffs 60. A suitable adhesive includes Findley H-2096 hot melt adhesive which is commercially available from Findley Adhesives, Inc., a business having offices located in Wauwatosa, Wis.

The concealment cuffs 60 hide the absorbent insert 80 and help prevent leakage of bodily exudates. In addition, the elasticity and conformability of the concealment cuffs 60 ensures that the absorbent insert 80 will remain between the cuffs 60, the outer cover 30 and the body of the wearer. As a result, it is not required that the outer cover 30 itself hold the absorbent insert 80 against the body of the wearer. Thus, the outer cover 30 of the present invention can be spaced away from the body and have a more garment-like appearance.

Figure 4:
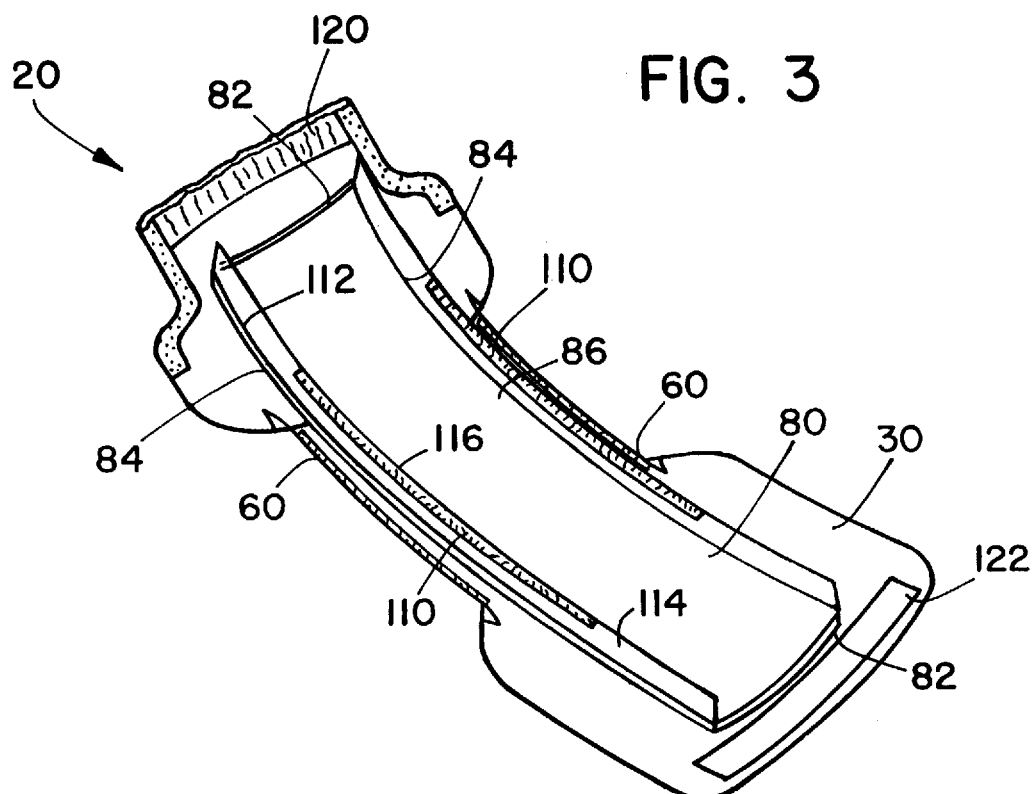
FIG. 4 representatively shows a perspective view of the disposable absorbent article of FIGS. 1 and 2 wherein the elastic members have contracted and gathered the edges of the disposable absorbent article.

As representatively illustrated in FIGS. 4 and 5, the absorbent insert 80 of the absorbent article 20 of the present invention defines a pair of longitudinally disposed end margins 82, a pair of laterally opposed side margins 84, and a crotch section 86 located between the end margins 82. The crotch section 86 of the absorbent insert 80 is configured to fit between the legs of the wearer and at least partially cover the lower torso of the wearer when in use. As a result, the crotch section 86 is generally the portion of the absorbent insert 80 which is configured to initially receive the body exudates from the wearer when in use. The absorbent insert 80 further defines a length 88 and a width 90.

The absorbent insert 80 is generally conformable and capable of absorbing and retaining body exudates. The absorbent insert 80 may have any of a number of shapes and sizes. For example, as representatively illustrated in FIGS. 4 and 12, the absorbent insert 80 may be rectangular, I-shaped or T-shaped. The size and absorbent capacity of the absorbent insert 80 should be compatible with the size of the intended wearer and the fluid loading imparted by the intended use of the absorbent article 20. Typically, it is desirable that the absorbent insert 80 have an absorbent capacity of at least about 300 grams of urine. It is generally preferred that the absorbent insert 80 be narrower in the crotch section 86 than in the end margins 82. It has been found that the absorbent insert 80 of the present invention is particularly useful when the width dimension 90 of the crotch section 86 of the absorbent insert 80 is from about 2.5 to about 10.2 centimeters (1.0 to about 4.0 inches), desirably no more than about 7.6 centimeters (3.0 inches) and more desirably no more than about 5.1 centimeters (2.0 inches). The narrow crotch width dimension 90 of the crotch section 86 of the absorbent insert 80 allows the absorbent insert 80 to better fit between the legs of the wearer.

The absorbent insert 80 of the present invention is suitably connected to the outer cover 30 to provide the disposable absorbent article 20. The absorbent insert 80 may be connected to the outer cover 30 along the entire length 88 of the absorbent insert 80 or only along a portion of the length 88. Desirably, only the end margins 82 of the absorbent insert 80 are connected to the outer cover 30 while the remainder of the absorbent insert 80 remains unconnected from the outer cover 30. For example, the absorbent insert 80 may be connected to the outer cover 30 along a length of no more than about 5.1 centimeters and desirably no more than about 1.3 centimeters at each of the end margins 82 of the absorbent insert 80. Desirably, the absorbent insert 80 is connected to the outer cover 30 over a total length which is less than about 15 percent and more desirably less than about 10 percent of the length 88 of the absorbent insert 80. In such a configuration, the absorbent insert 80 more readily conforms to the body and movements of the wearer in use without adversely affecting the garment-like appearance of the outer cover 30. In a particular aspect, the length of the absorbent insert 80 between the connected portions of the end margins 82 which remains unconnected to the outer cover 30 is less than the length of the outer cover 30 between the connected portions. In such a configuration, at least the crotch region 86 of the absorbent insert 80 maintains a spaced away relationship from the outer cover 30 when in use.

The absorbent insert 80 may be suitably connected to the outer cover 30 to form the absorbent article 20 using any means known to those skilled in the art. For example, the absorbent insert 80 may be bonded to the outer cover 30 using adhesive, thermal or ultrasonic bonding techniques known to those skilled in the art. Alternatively, the absorbent insert 80 may be connected to the outer cover 80 using conventional fasteners such as buttons, hook and loop type fasteners, adhesive tape fasteners, and the like.

Figure 7:
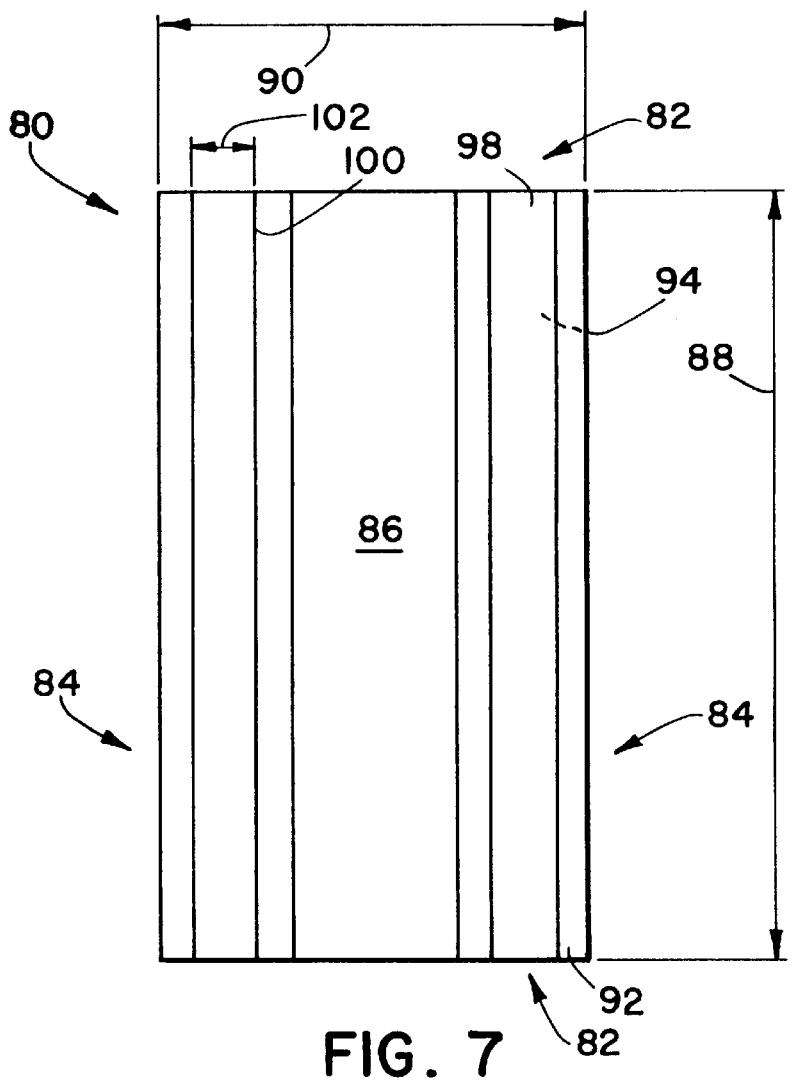
FIG. 7 representatively shows a plan view of an example of an absorbent insert of the disposable absorbent article according to the present invention in a stretched and laid flat condition.
Figure 8:
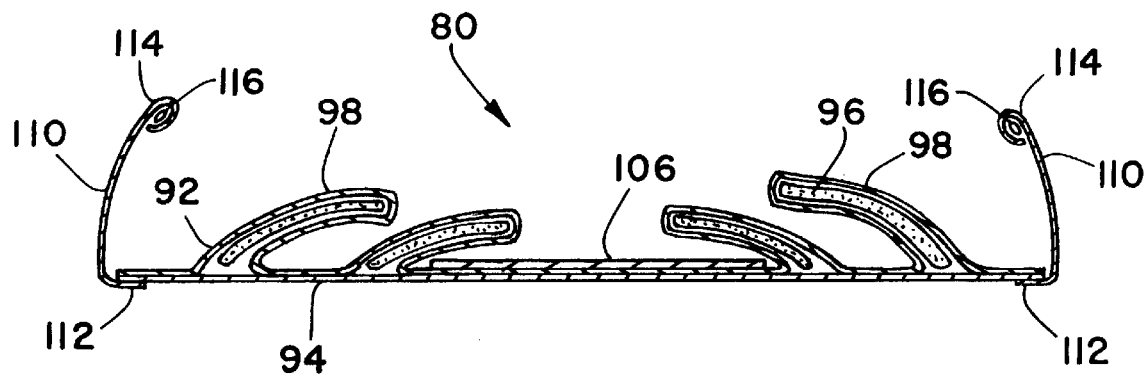
FIG. 8 representatively shows a section view of the absorbent insert of FIG. 7.
Figure 9:
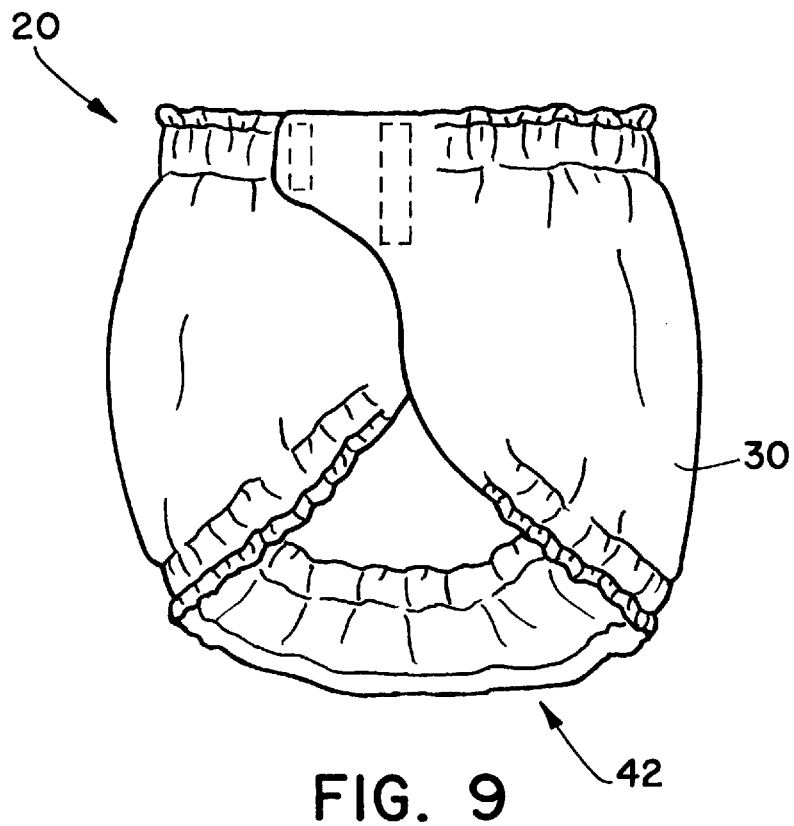
FIG. 9 representatively shows a side elevational view of another example of a disposable absorbent article according to the present invention.
Figure 10:
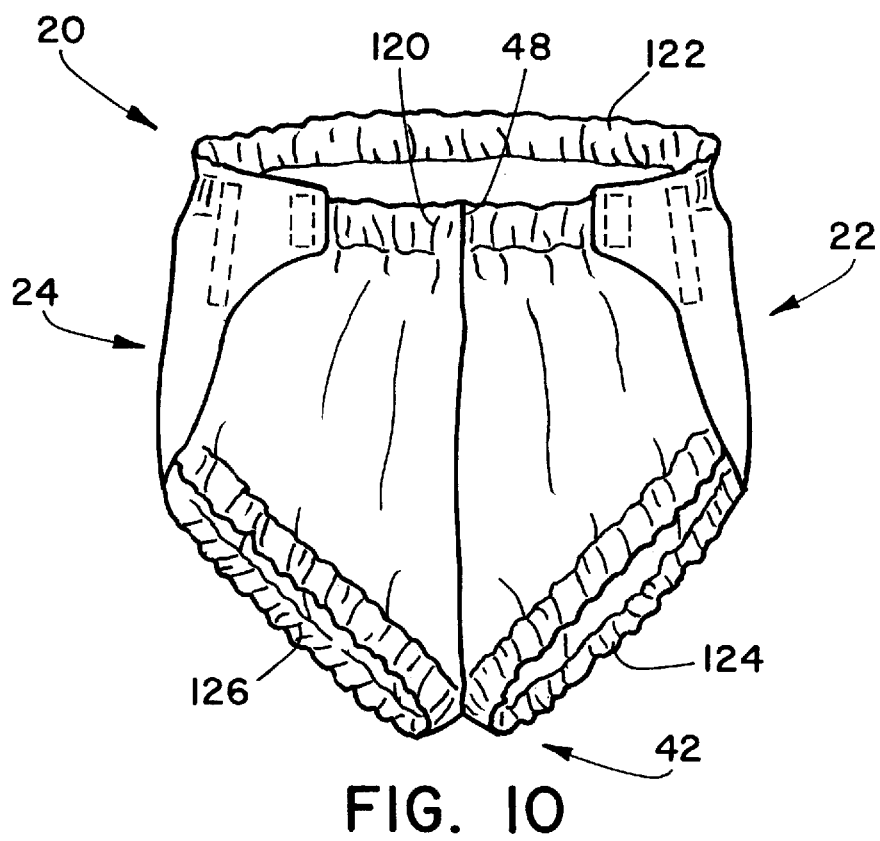
FIG. 10 representatively shows a front elevational view of the disposable absorbent article of FIG. 9.
Figure 11:
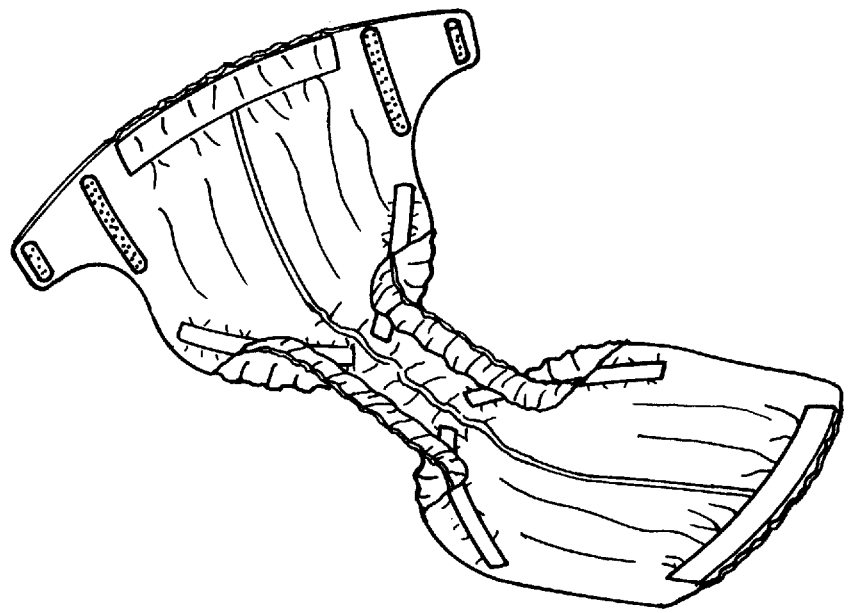
FIG. 11 representatively shows a perspective view of the outer cover of the disposable absorbent article of FIGS. 9 and 10 wherein the absorbent insert has been removed and the elastic members have contracted and gathered the edges of the outer cover.
Figure 12:
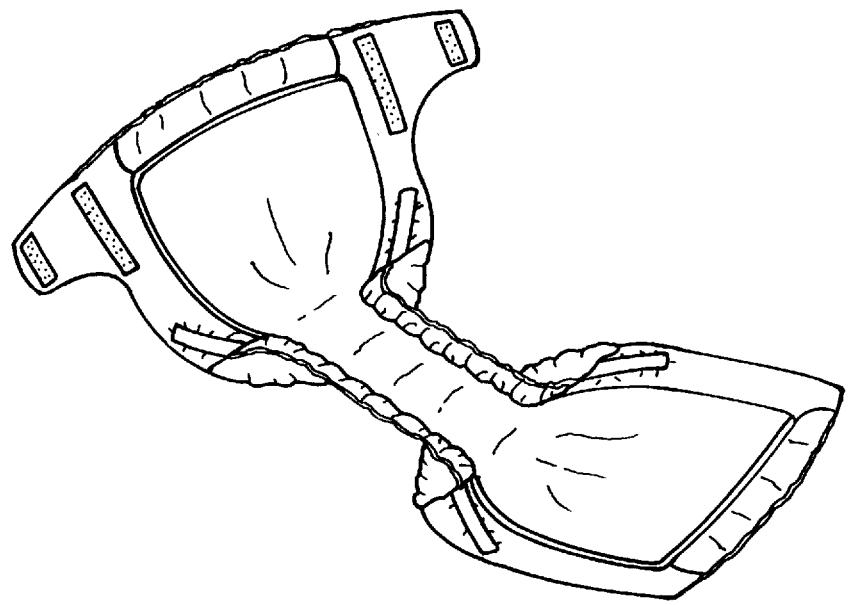
FIG. 12 representatively shows a perspective view of the disposable absorbent article of FIGS. 9 and 10 wherein the elastic members have contracted and gathered the edges of the disposable absorbent article.

FIGS. 7 and 8 representatively illustrate an example of an absorbent insert 80 according to the present invention which includes a bodyside liner 92, a backsheet 94 which is connected to the bodyside liner 92 in a superposed relation, and an absorbent core 96 which is located between the bodyside liner 92 and the backsheet 94. In alternative configurations wherein the outer cover 60 is at least partially resistant to the flow of liquids therethrough, the backsheet 94 may optionally be omitted from the absorbent insert 80.

The bodyside liner 92 of the absorbent insert 80, as representatively illustrated in FIGS. 7 and 8, suitably presents a bodyfacing surface which is intended to be worn adjacent the body of the wearer and is compliant, soft feeling and nonirritating to the wearer's skin. Further, the bodyside liner 92 may be less hydrophilic than the absorbent core 96, to present a relatively dry surface to the wearer, and may be sufficiently porous to be liquid permeable, permitting liquid to readily penetrate through its thickness. A suitable bodyside liner 92 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 92 is suitably employed to help isolate the wearers skin from fluids held in the absorbent core 96 of the absorbent insert 80.

Various woven and nonwoven fabrics can be used for the bodyside liner 92. For example, the bodyside liner may be composed of a meltblown or spunbonded web of polyolefin fibers The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 92 comprises a nonwoven, spunbond, polypropylene fabric composed of about 2.8–3.2 denier fibers formed into a web having a basis weight of about 22 grams per square meter and a density of about 0.06 grams per cubic centimeter. The fabric is surface treated with about 0.28 weight percent of a surfactant commercially available from Rohm and Haas Co. under the trade designation Triton X-102.

The backsheet 94 of the absorbent insert 80, as representatively illustrated in FIGS. 7 and 8, may suitably be composed of a material which is either liquid permeable or liquid impermeable. It is generally preferred that the backsheet 94 be formed from a material which is substantially impermeable to fluids. For example, a typical backsheet can be manufactured from a thin plastic film or other flexible liquid-impermeable material. For example, the backsheet 94 may be formed from a polyethylene film having a thickness of from about 0.012 millimeter (0.5 mil) to about 0.051 millimeter (2.0 mils). The backsheet 94 may also comprise a film layer having a nonwoven web laminated to the outer surface thereof, such as a spunbond web of polyolefin fibers. The backsheet 94 may also be constructed of a material which is similar to the material comprising the outer cover, such as an STL material. Further, the backsheet 94 may be formed of a woven or nonwoven fibrous web layer which has been totally or partially constructed or treated to impart a desired level of liquid impermeability to selected regions that are adjacent or proximate the absorbent core 96. Still further, the backsheet 94 may optionally be composed of a micro-porous "breathable" material which permits vapors to escape from the absorbent core 96 while still preventing liquid exudates from passing through the backsheet 94.

The bodyside liner 92 and backsheet 94 are generally adhered to one another so as to form a pocket in which the absorbent core 96 is located to provide the absorbent insert 80. The bodyside liner 92 and backsheet 94 may be adhered directly to each other around the outer periphery of the absorbent insert 80 by any means known to those skilled in the art such as adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the bodyside liner 92 to the backsheet 94. It should be noted that both the bodyside liner 92 and the backsheet 94 need not extend completely to the outer periphery of the absorbent insert 80. For example, the backsheet 94 may extend to the outer periphery of the absorbent insert 80 while the bodyside liner 92 may be attached to the backsheet 94 inboard of the outer periphery of the absorbent insert 80, or more towards the longitudinal centerline 26, of the absorbent article 20. In alternative configurations, especially wherein the backsheet 94 is omitted, the bodyside liner 92 may be suitably adhered directly to the absorbent core 96.

The absorbent core 96, as representatively illustrated in FIGS. 7 and 8, is positioned between the bodyside liner 92 and the backsheet 94 to form the absorbent insert 80. The absorbent core 96 is desirably conformable and capable of absorbing and retaining body exudates. The absorbent core 96 may have any of a number of shapes and sizes. For example, the composite absorbent core may be rectangular, I-shaped or T-shaped. It is generally preferred that the absorbent core 96 be narrower in the crotch section 86 of the absorbent insert 80. The size of the absorbent core 96 should be compatible with the size of the intended wearer and the desired absorbent capacity of the absorbent insert 80.

In a particular embodiment, as representatively illustrated in FIGS. 7 and 8, the absorbent core 96 of the absorbent insert 80 is desirably a plurality of absorbent strips 98 which extend along the longitudinal length 88 of the absorbent insert 80. The absorbent strips 98 are generally rectangular in shape and define a length, a width, a thickness and a pair of opposite longitudinal side edges. The absorbent strips 98 are configured to pivot about one of the longitudinal side edges while the opposite longitudinal side edge of the absorbent strips 98 remains free to move. The absorbent core 96 may include any number of absorbent strips 98 which provides the desired containment of body exudates. For example, as illustrated in FIG. 7 and 8, the absorbent core 96 may include four longitudinally extending absorbent strips 98. In alternative configurations, the absorbent core 96 may include from 1 to about 10 absorbent strips 98. The arrangement of the absorbent strips 98 provides channels between each strip to better distribute and contain fluid exudates. Moreover, the arrangement of the strips 98 provides a greater surface area in contact with the body exudates to more effectively absorb and contain the exudates.

The absorbent strips 98 are also very conformable in the crotch section 86 of the absorbent insert 80. As representatively illustrated in FIG. 8, the absorbent strips 98 are arranged such that they may overlap each other in a shingled arrangement when subjected to a lateral force such as exerted by the legs of a wearer in use. Accordingly, the absorbent strips 98 provide an absorbent core 96 which is readily adaptable to change dimensions depending upon the position and movement of the wearer. For example, if the absorbent core 96 includes four absorbent strips 98, each of which has a width of 2.0 centimeters, the effective width of the absorbent core 96 may be from about 4.0 to about 8.0 centimeters depending upon the amount of overlap of each strip 98 with the adjacent strip. Thus, when compared to conventional solid, rectangular-shaped absorbent cores, the use of absorbent strips 98 such as is illustrated in FIGS. 7 and 8 provides an absorbent core 96 for an absorbent article which has an improved fit especially in the crotch region. Such improved fit may enhance the appearance of the absorbent article 20 and performance of the absorbent core 96.

The absorbent strips 98 may have any length and width which provides sufficient absorptive capacity. Desirably, the absorbent strips 98 extend along the entire length 88 of the absorbent insert 80 and have a width of from about 1.3 to about 5.1 centimeters. Various configurations for the absorbent strips 98 are described in U.S. patent application Ser. No. 08/476,742 of S. Gryskiewicz et al., entitled ABSORBENT ARTICLE INCLUDING LIQUID CONTAINMENT BEAMS AND LEAKAGE BARRIERS, and filed Jun. 7, 1995 (Attorney Docket No. 12,187); the disclosure of which is hereby incorporated by reference in a manner that is consistent herewith.

The absorbent core 96 of the absorbent insert 80 may suitably comprise various types of wettable, hydrophilic fibrous materials. Examples of suitable materials include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent core 96 may also comprise selected blends of the various types of fibers mentioned above.

In a particular aspect of the invention, the absorbent core 96 may include a matrix of hydrophilic fibers, such as a web of cellulosic fibers, mixed with particles of a high-absorbency material such as that commonly known as superabsorbent material. As used herein, the term "high-absorbency material" refers to materials that are capable of absorbing at least 10 times their own weight in liquid. In a particular embodiment, the absorbent core 96 comprises a mixture of superabsorbent hydrogel-forming particles and wood pulp fluff. The wood pulp fluff may be exchanged with synthetic, polymeric, meltblown fibers or with a combination of meltblown fibers and natural fibers. The high-absorbency material may be substantially homogeneously mixed with the hydrophilic fibers or may be nonuniformly mixed. The high-absorbency material may also be arranged in a generally discrete layer within the matrix of hydrophilic fibers. Alternatively, the absorbent core 96 may comprise a laminate of fibrous webs and high-absorbency material or other suitable means of maintaining a high-absorbency material in a localized area.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like. Conglomerates of particles of high-absorbency material may also be used. An example of a superabsorbent polymer suitable for use in the present invention is a superabsorbent polymer designated IM5000 which is commercially available from Hoechst-Celanese, a business having offices in Portsmouth, Va. Other suitable high-absorbency materials may include superabsorbent polymers which are commercially available from Dow Chemical Corp., a business having offices in Midland, Mich.

As a general rule, the high-absorbency material is present in the absorbent core 96 of the present invention in an amount of from about 5 to about 95 weight percent and desirably from about 10 to about 60 weight percent based on the total weight of the absorbent core 96. The distribution of the high-absorbency material within the different portions of the absorbent core 96 can vary depending upon the intended end use of the absorbent core 96.

As representatively illustrated in FIGS. 1–8, the absorbent insert 80 of the disposable absorbent article 20 may include a pair of containment flaps 110 which are configured to provide a barrier to the lateral flow of body exudates. The containment flaps 110 may be located along the laterally opposed side margins 84 of the absorbent insert 80. Each containment flap 110 defines an attached edge 112 and an unattached edge 114. Each of the containment flaps 110 may also include at least one elongated elastic member 116 which is adhered to the unattached edge 114 of the containment flap 110 and configured to gather the unattached edge 114 and form a seal against the body of the wearer when in use. The containment flaps 110 may extend longitudinally along the entire length 88 of the absorbent insert 110 or may only extend partially along the length of the absorbent insert 80. When the containment flaps 110 are shorter in length than the absorbent insert 80, the containment flaps 110 can be selectively positioned anywhere along the side margins 84 of the absorbent insert 80. In a particular aspect of the invention, the containment flaps 110 extend along the entire length 88 of the absorbent insert 80 to better contain the body exudates.

The containment flaps 110 can be made from any material which provides the desired barrier against the flow of body exudates. For example, the containment flaps 110 may be constructed of a material which is similar to the material comprising the outer cover 30. Other conventional materials, such as polymer films, may also be employed. In a particular aspect, the containment flaps 110 may be constructed of a STL material having a basis weight of about 73 grams per square meter and comprising a meltblown layer of meltblown polypropylene fibers between two spunbond layers of polypropylene fibers.

Each containment flap 110 is attached to the side margins 84 of the absorbent insert 80 such that the containment flaps 110 provide a barrier to the lateral flow of body exudates. The attached edge 112 of each of the containment flaps 110 is attached to the side margins 84 of the absorbent insert 80 while the unattached edge 114 remains unattached from the absorbent insert 80 in at least the crotch section 86 of the absorbent insert 80. The attached edge 112 of the containment flaps 110 may be attached to the absorbent insert 80 in any of several ways which are well known to those skilled in the art. For example, the attached edge 112 of the flaps 110 may be ultrasonically bonded, thermally bonded or adhesively bonded to the outer cover 30. In a particular aspect, the unattached edge 114 of each of the containment flaps 110 remains unattached from the side margins 84 of the absorbent insert 80 along substantially the entire length of the unattached edge 114 to provide improved performance. Alternatively, the containment flaps 110 may be integral with the backsheet 94 of the absorbent insert 80.

Each containment flap 110 is also configured such that the unattached edge 114 of the containment flap 110 tends to position itself in a spaced relation away from the absorbent insert 80 toward a generally upright and perpendicular configuration, especially in the crotch section 86 when in use. As representatively illustrated in FIGS. 7 and 8, the unattached edge 114 of each containment flap 110 is desirably spaced away from the absorbent insert 80 when in use thereby providing a barrier to the lateral flow of body exudates. Desirably, the unattached edge 114 of each containment flap 110 maintains a contacting relationship with the body of the wearer while the absorbent insert 80 may be spaced away from the body of the wearer when in use. Typically, an elastic member 116 is attached to the unattached edge 114 of each containment flap 110 to maintain the spaced away relationship between the unattached edge 114 and the absorbent insert 80. For example, the elastic member 116 may be attached to the unattached edge 114 in an elastically contractible condition such that the contraction of the elastic member 116 gathers or contracts and shortens the unattached edge 114 of the containment flap 110.

Materials suitable for use as the elastic member 116 of the containment flaps 110 include those described above as being suitable for use as the elastic member 66 in the concealment cuffs 60. In a particular aspect of the invention, the elastic members 116 may be composed of a plurality of individual strands of 620 decitex Lycra® which are commercially available from E. I. DuPont de Nemours Co. The containment flaps 110 may include from about 1 to about 10 elastic strands along the unattached edge 114. The elastic members 116 may be elongated prior to being attached to the unattached edge 114 of the containment flaps 110. For example, the elastic members 116 may be elongated at least about 75 percent and desirably from about 100 to about 150 percent before being attached such that the elastic members 116 gather the unattached edge 114 of the containment flaps 110. Desirably, the elastic members 116 are configured to gather and maintain the unattached edge 114 in a contacting relationship with the wearer's body when in use to effectively provide a seal against the lateral flow of body exudates.

Alternative constructions and arrangements for containment flaps 110 are described in U.S. Pat. No. 4,704,116 issued Nov. 3, 1987, to K. Enloe the disclosure of which is hereby incorporated by reference in a manner that is consistent herewith.

The absorbent article 20 of the different aspects of the present invention may further include a distribution or surge layer which is configured to quickly collect, temporarily hold, and subsequently distribute liquid surges. For example, as representatively illustrated in FIGS. 7 and 8, the absorbent article 20 may include a surge layer 106 which can help prevent liquid exudates from pooling and collecting on the absorbent insert 80 thereby improving the overall uptake rate of the absorbent article 20. The surge layer 106 is positioned in the absorbent article 20 to be in liquid communication with the absorbent core 96 of the absorbent insert 80. In the illustrated embodiment, the surge layer 106 is located on the bodyside liner 92 of the absorbent insert 80 and is configured to be in contact with the wearer's body. Alternatively, the surge layer may be located between the bodyside liner 92 and the absorbent core 96 of the absorbent insert 80. The shown configuration of the surge layer 106 is operably connected to the bodyside liner 92 of the absorbent insert 80 with a conventional pattern of adhesive. The amount of adhesive should be sufficient to provide the desired level of bonding but should be low enough to avoid excessively restricting the movement of liquids between the layers.

Various woven and nonwoven fabrics can be used to construct the surge layer 106. For example, the surge layer 106 may be composed of a meltblown or spunbonded web of polyolefin fibers. The surge layer 106 may also be a bonded carded web or an airlaid web composed of natural and synthetic fibers. In desired configurations of the invention, the surge layer 106 can include natural fibers, synthetic fibers, such as synthetic polymer fibers, and combinations thereof. The surge layer 106 can, for example, be composed of polyolefin fibers, and in particular configurations the fibers can include bicomponent fibers. For example, polypropylene/polyethylene bicomponent fibers may be employed in the surge layer 106.

The surge layer 106 can be of any desired shape consistent with the absorbency requirements of the absorbent insert 80. Suitable shapes include, for example, circular, rectangular, triangular, trapezoidal, oblong, dog-boned, hourglass-shaped, or oval. In a particular embodiment, the surge layer 106 is rectangular shaped. The surge layer 106 may extend over the complete length 88 of the absorbent insert 80 or may extend over only a portion of the length 88 of the absorbent insert 80. Desirably, the surge layer 106 is approximately centered about the longitudinal centerline of the absorbent insert 80 and positioned in at least the crotch section 86 of the absorbent insert 80.

Additional details regarding materials useful for the surge layer 106 and suitable techniques for incorporating the surge layer 106 in absorbent articles are set forth in U.S. patent application Ser. No. 206,986 of C. Ellis and D. Bishop, entitled, FIBROUS NONWOVEN WEB SURGE LAYER FOR PERSONAL CARE ABSORBENT ARTICLES AND THE LIKE, and filed Mar. 4, 1994 (Attorney docket No. 11,256); U.S. patent application Ser. No. 206,069 of C. Ellis and R. Everett, entitled, IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); U.S. patent application Ser. No. 310,186 of F. Chen et al., entitled, WET RESILIENT PAPER SHEETS, and filed Sep. 21, 1994 (Attorney docket No. 11,700); the disclosures of which are hereby incorporated by reference in a manner that is consistent herewith.

The absorbent article of the different aspects of the present invention further includes a fastening means for securing the absorbent article about the waist of the wearer. The fastening means are typically applied to the outermost corners of the side portions 22 and 24 of the absorbent article 20 to provide a means for holding the article 20 on the wearer. Typically, the fastening means are located on the outer cover 30 of the absorbent article 20 and configured to be refastenable. The use of fasteners which are refastenable or releasably engageable allows for ease of securing and removing the article from the waist of the wearer. As representatively illustrated in FIGS. 1–5, the disposable absorbent article 20 of the present invention may include a first fastener 70 which is releasably engageable with a second fastener 72. For example, a first fastener 70 may be located along the side edge of one of the waist regions 38 of each of the side panels 44 and 46 of the outer cover 30 and a second fastener 72 may be located along the side edge of the opposite waist region 40 of each side panel 44 and 46 of the outer cover. In such a configuration, the first fastener 70 and second fastener 72 on each side panel 44 and 46 are releasably engageable together along a side seam to maintain the article 20 on the wearer. When the fasteners 70 and 72 are releasably engaged together, the side regions 34 and 36 of the outer cover 30 encircle the legs of the wearer thereby defining the leg openings 54 and 56, respectively.

Desirably, the design of the outer cover 30 is such that the absorbent article may be reversible about the wearer. For example, each side panel 44 and 46 may be substantially symmetrical and substantially identical to each other. Accordingly, the fasteners 70 and 72 may be located more on the front of the wearer or on the back of the wearer depending upon the users preference. By attaching the absorbent article about the wearer such that the fasteners are located more near the back of the wearer, the wearer is less apt to be able to disengage the fasteners 70 and 72 in use. Such a configuration is particularly desirable when the absorbent article 20 is intended to be worn by an infant.

Suitable fastening means are well known to those skilled in the art and can include tape tab fasteners, hook and loop fasteners, mushroom fasteners, snaps, pins, belts and the like, and combinations thereof. For example, as representatively illustrated in FIGS. 1–6, the first fastener 70 may be a hook type fastener and the second fastener 72 may be a loop type fastener. Typically, the fasteners 70 and 72 are separate elements which are attached to the absorbent article 20. Alternatively, the fasteners 70 and 72 may be integral with other components of the absorbent article. For example, when the first fastener 70 is a hook type fastener, the second fastener 72 may be the outer cover 30 or a separate loop element attached to the outer cover 30. Desirably, the first fastener 70 is a hook type fastener which is releasably engageable with the outer cover 30. Such an arrangement provides the ability to vary the size of the waist opening in very small increments over a wide range to fit the waist of the wearer.

The fasteners 70 and 72 may have any shape and size which provides the desired fastening of the absorbent article 20 about the waist of the wearer. For example, FIGS. 1–6 and 9–12 representatively illustrate alternative configurations for the fasteners 70 and 72. Desirably, the fasteners 70 and 72 engage along a length, as measured parallel to the longitudinal centerline 26 of the article 20, which is at least about 5.1 centimeters and desirably at least about 10.2 centimeters to maintain the absorbent article about the waist of the wearer and ensure that the side panels 44 and 46 of the outer cover 30 remain in the desired position.

The disposable absorbent article of the different aspects of the present invention may further include elastics at the waist opening 58 and leg openings 54 and 56 to further prevent the leakage of body exudates. For example, as representatively illustrated in FIGS. 1–12, the absorbent article 20 of the present invention may include a pair of waist elastic members 120 and 122 which are connected to the outer cover 30 and configured to gather and contract the waist regions 38 and 40 of the outer cover 30. As illustrated in FIGS. 9–12, the disposable absorbent article 20 may further include a pair of leg elastics 124 and 126 which are connected to the laterally opposed side regions 34 and 36 in the crotch region 42 of the outer cover 30. The waist elastics 120 and 122 and leg elastics 124 and 126 are generally adapted to fit about the waist and legs of a wearer, respectively, in use to maintain a positive, contacting relationship with the wearer to effectively reduce or eliminate the leakage of body exudates from the absorbent article 20. In a particular aspect, the outer cover 30 of the absorbent article 20 does not include leg elastics 124 and 126 such that the outer cover maintains a more garment-like appearance.

Materials suitable for use as the leg elastics 124 and 126 and the waist elastics 120 and 122 are well known to those skilled in the art. Exemplary of such materials are sheets or strands or ribbons of a polymeric, elastomeric material which are adhered to the outer cover 30 in a stretched position, or which are attached to the outer cover 30 while the outer cover is pleated, such that elastic constrictive forces are imparted to the outer cover 30. The leg and waist elastics may also include such materials as polyurethane, synthetic and natural rubber. In a particular aspect of the invention, the elastics may be composed of individual strands of 620 decitex Lycra® which are commercially available from E. I. DuPont de Nemours Co. When individual strands of elastic are used, the waist and leg elastics may include any suitable number of elastic strands to provide containment of the body exudates. For example, the waist elastics 120 and 122 and leg elastics 124 and 126 may include from about 1 to about 10 elastic strands. The waist and leg elastics may be elongated prior to being attached to the outer cover 30. For example, the waist and leg elastics may be elongated at least about 150 percent and desirably from about 200 to about 500 percent before being attached such that the elastics gather the outer cover 30 when relaxed. The waist elastics 120 and 122 and leg elastics 124 and 126 may be joined to the outer cover 30 by any means known to those skilled in the art 38. For example, adhesive, thermal or ultrasonic bonding techniques may be used to join the elastics to the outer cover. A suitable adhesive includes Findley H-2096 hot melt adhesive which is commercially available from Findley Adhesives, Inc.

The different aspects of the present invention can advantageously provide a disposable absorbent article which has a garment-like appearance. As a result, the disposable absorbent article of the present invention effectively contains body exudates while maintaining an optimum fit and an aesthetically pleasing appearance. Moreover, the crotch region of the disposable absorbent article of the present invention does not bunch up as conventional absorbent articles have. As a result, the absorbent article may have a reduced level of leakage from the crotch region.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

I claim:

1. A disposable absorbent article which defines a first side portion, a second side portion, and a longitudinal centerline between said side portions, said absorbent article comprising:

a) an outer cover which defines a length, a pair of laterally opposed side regions, a pair of longitudinally opposed waist regions, and a crotch region which extends between and connects said waist regions, said outer cover comprising a first side panel which is located in said first side portion of said absorbent article and a second side panel which is located in said second side portion of said absorbent article wherein an edge of said first side panel is connected to an edge of said second side panel to provide a seam which extends along said longitudinal centerline between said side portions of said absorbent article and wherein said seam on each of said side panels defines a "U" shape when said side panel is in a laid flat configuration; and b) an absorbent insert which is connected to said outer cover, wherein each of said side panels of said outer cover further comprises a first fastener which is located on one of said waist regions and a second fastener which is located on said opposite waist region and wherein said first fastener and said second fastener on each of said side panels are releasably engageable together.

2. The absorbent article of claim 1 wherein said opposite waist regions on each side panel are releasably engageable together to define a pair of leg openings in said outer cover.

3. The absorbent article of claim 1 wherein said first fastener and said second fastener are complimentary hook and loop type fasteners.

4. The absorbent article of claim 1 wherein said seam extends along substantially said entire length of said outer cover.

5. The absorbent article of claim 1 wherein said seam is substantially continuous.

6. The absorbent article of claim 1 wherein said edges of said side panels overlap along said seam to provide a seam width of at least about 0.64 centimeters.

7. The absorbent article of claim 1 wherein said outer cover defines a crotch length in said crotch region which is at least about 15 percent of said length of said outer cover.

8. The absorbent article of claim 1 wherein said outer cover defines a crotch length in said crotch region which is at least about 8 centimeters.

9. The absorbent article of claim 1 wherein said outer cover is made from a nonwoven material.

10. The absorbent article of claim 1 wherein said first side panel and said second side panel define a substantially identical pattern.

11. The absorbent article of claim 1 and further comprising a pair of concealment cuffs which are located along said side regions of said outer cover, wherein each concealment cuff defines a fixed edge which is connected to said outer cover and a free edge which remains unconnected to said outer cover in at least said crotch region of said outer cover.

12. The absorbent article of claim 11 wherein said free edge of each of said concealment cuffs includes at least one elastic member which is configured to maintain said free edge in a spaced away relationship from said outer cover in at least said crotch region of said outer cover.

13. The absorbent article of claim 12 wherein said elastic member is connected to said free edge of said concealment cuff at an elongation of no more than about 150 percent.

14. The absorbent article of claim 12 wherein said elastic member exerts a tension of no more than about 150 grams on said free edge of said concealment cuff when said free edge is fully extended.

* * * * *